(12) United States Patent
Licht et al.

(10) Patent No.: US 6,428,466 B1
(45) Date of Patent: Aug. 6, 2002

(54) SPA CAPSULE

(75) Inventors: Allen Licht, Philadelphia, PA (US); Alex Spivak, Hallandale; Ilya Spivak, Hollywood, both of FL (US)

(73) Assignee: Simulated Environment Concepts, Inc., Philadelphia, PA (US)

( * ) Notice: Subject to any disclaimer, the term of this patent is extended or adjusted under 35 U.S.C. 154(b) by 0 days.

(21) Appl. No.: 09/783,737

(22) Filed: Feb. 14, 2001

(51) Int. Cl.[7] .............................................. A61M 21/00
(52) U.S. Cl. ...................................................... 600/27
(58) Field of Search ............................. 600/27, 28, 26, 600/21; 601/52, 58, 16, 116; 607/82, 88, 91

(56) References Cited

U.S. PATENT DOCUMENTS

| | | | | |
|---|---|---|---|---|
| 3,826,250 A | * | 7/1974 | Adams | 600/28 |
| 4,112,943 A | | 9/1978 | Adams | |
| 4,751,919 A | | 6/1988 | Thomsen | |
| 5,101,809 A | * | 4/1992 | Daffer et al. | 600/27 |
| 5,219,322 A | * | 6/1993 | Weathers | 600/27 |
| 5,266,070 A | * | 11/1993 | Hagiwara et al. | 600/27 |
| 5,645,578 A | * | 7/1997 | Daffer et al. | 600/27 |
| 5,891,186 A | * | 4/1999 | Daffer et al. | 600/27 |

* cited by examiner

*Primary Examiner*—Kevin Shaver
*Assistant Examiner*—Brian Szmal
(74) *Attorney, Agent, or Firm*—McHale & Slavin, P.A.

(57) ABSTRACT

A spa capsule has a cabinet and a hinged lid forming an enclosed space for accommodating a person. Within the enclosed space an environment is simulated by stimulating the auditory, olfactory, optic and tactile senses of the person.

19 Claims, 6 Drawing Sheets

SPA CAPSULE

FIELD OF THE INVENTION

This invention relates to the field of physical therapy and in particular, to devices used to relieve stress and soothe the senses by applying desirable sensations to the body.

BACKGROUND OF THE INVENTION

The use of aromatic oils, fragrances, baths and massage for personal well being is quite ancient. Further, the viewing of beautiful pictures and listening to music. has long been recognized as beneficial to the mood of people.

However, in the modern world, these past times have become less accessible to most of the people either because of the lack of artisans capable of performing the necessary acts or the expense and time required to attend such facilities. To combat these modern day societal shortcomings, machines have been employed in an attempt to relieve the stresses of the day. There are different mechanical devices for massage, for tanning and for simulated weightlessness.

What is lacking in the art is a comprehensive approach to the overall benefits of using several different biological senses to ameliorate the effects of stress and trauma.

DESCRIPTION OF THE PRIOR ART

Known prior art exists in the field of hydrotherapy including devices related to water massage. For example, expired U.S. Pat. No. 4,112,943 discloses the use of an enclosed bag having a pulsed flow of water into the bag. The device may be placed on the body at a desired treatment location for muscle injuries and the like. U.S. Pat. No. 4,751,919 discloses a water jet massage apparatus which supports a supine person covered with a waterproof blanket. The water massage is carried out without the person becoming wet. Still other know patents disclose the use of a dry water massage to a sitting person.

SUMMARY OF THE INVENTION

In a preferred embodiment, a spa capsule is formed from a cabinet having a hinged lid forming an enclosed space for accommodating a person. Within the enclosed space an environment is simulated by stimulating the auditory, olfactory, optic and tactile senses of the person.

The spa capsule partially encloses a person's body to provide a simulated environment by stimulating the olfactory senses by inducing certain aromatic substances to release odors within the enclosed space. The capsule includes a bed extending from the head of a person to the feet providing support in the prone or supine position. The enclosure includes a means for stimulating the auditory senses by conveying certain sounds into the enclosed space and stimulating the optic senses by conveying visual images into the enclosed space either simultaneously, sequentially or in various sequences.

The tactile senses are addressed by a massage with jets of water applying gentle pressure to the body of the prone or supine user. The jets are contained within a flexible enclosure to allow for a dry massage. The water jet enclosure closely contacts the body and is movable about the length of the spa to provide stimulation to most of the body.

Accordingly, it is an objective of the instant invention to teach the stimulation of several biological senses in an enclosed environment for therapeutic results.

It is a further objective of the instant invention to teach the use of a cabinet enclosing a person in a selected environment which includes stimulation of the auditory, olfactory, optic and tactile senses.

It is yet another objective of the instant invention to teach the application of selected aromas, sounds, pictures and physical contact to a person in a particular program.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
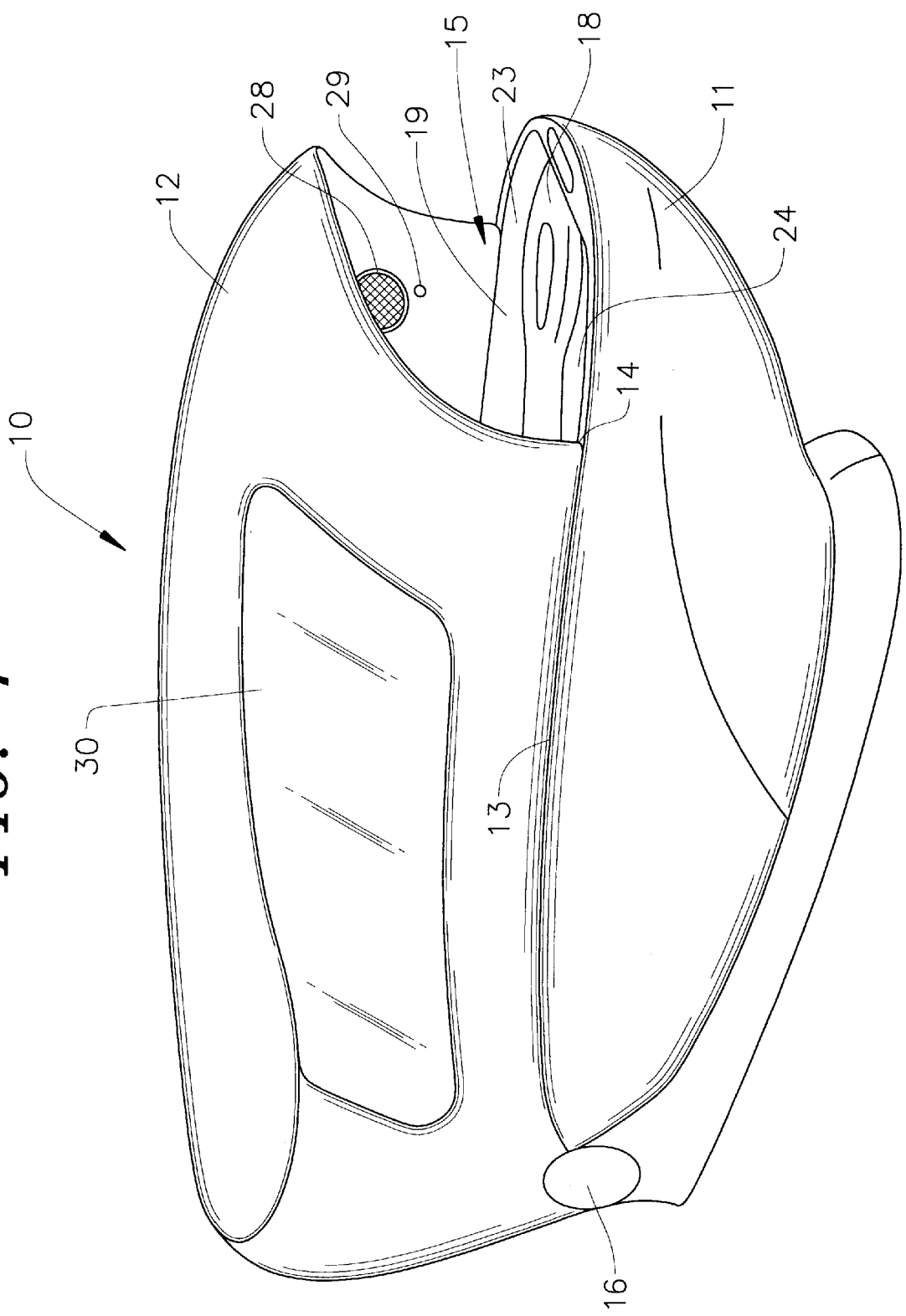
FIG. 1 shows a perspective of the spa of the invention.

The spa capsule 10 of FIG. 1 has a cabinet 11 and a lid 12. As shown, the cabinet and top are egg-shaped in the closed position defining an enclosed space. The peripheral edges 13 and 14 of the lid 12 and cabinet 11 contact each other and form a seal when the lid is closed. The smaller end of the egg-shaped spa accommodates the feet of a person lying inside the spa. The lid is somewhat shorter than the cabinet and the larger end of the lid is open. The opening 15 allows the person in the spa to communicate with the space outside the spa. The cabinet and lid may be molded from a high strength polymer or made from another lightweight material, such as aluminum or other metal.

The cabinet and top are hinged together at 16 to allow a person to enter the spa when the lid is in the open or raised position. The hinge may have a spring loaded mechanism 61 such that the top will automatically raise when lifted from the cabinet. When raised it will remain so until force is applied to close the lid. The cabinet is mounted on swiveling casters 59 which permit maneuvering the spa in confined spaces.

Figure 2:
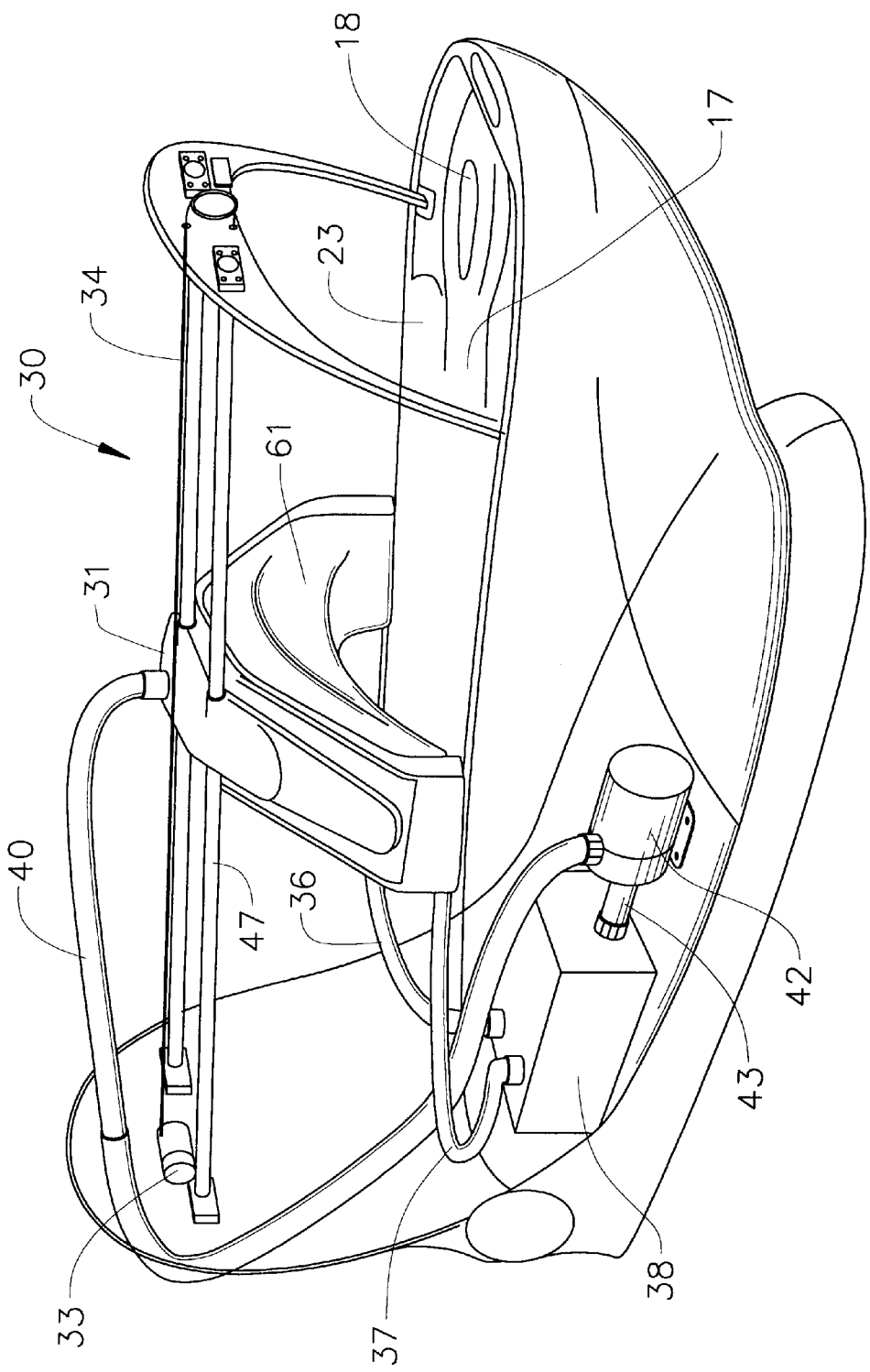
FIG. 2 shows a perspective with exterior portions and the lid removed.

Inside the cabinet is a bed 17 for supporting a supine person. As seen in FIG. 2, the head end of the bed has an aperture 18 which accommodates the face of a person when lying in the prone position. On both sides of the aperture 18, there are arm rests 23 and 24. The support surfaces of the arm rests are positioned somewhat lower than the central portion of the bed containing the aperture 18 to permit a less stressful orientation for the shoulders in the prone position. The bed may include a pad 19 for comfort. The bed 17 and pad 19 may have an electrically powered vibratory function (not shown).

Figure 3:
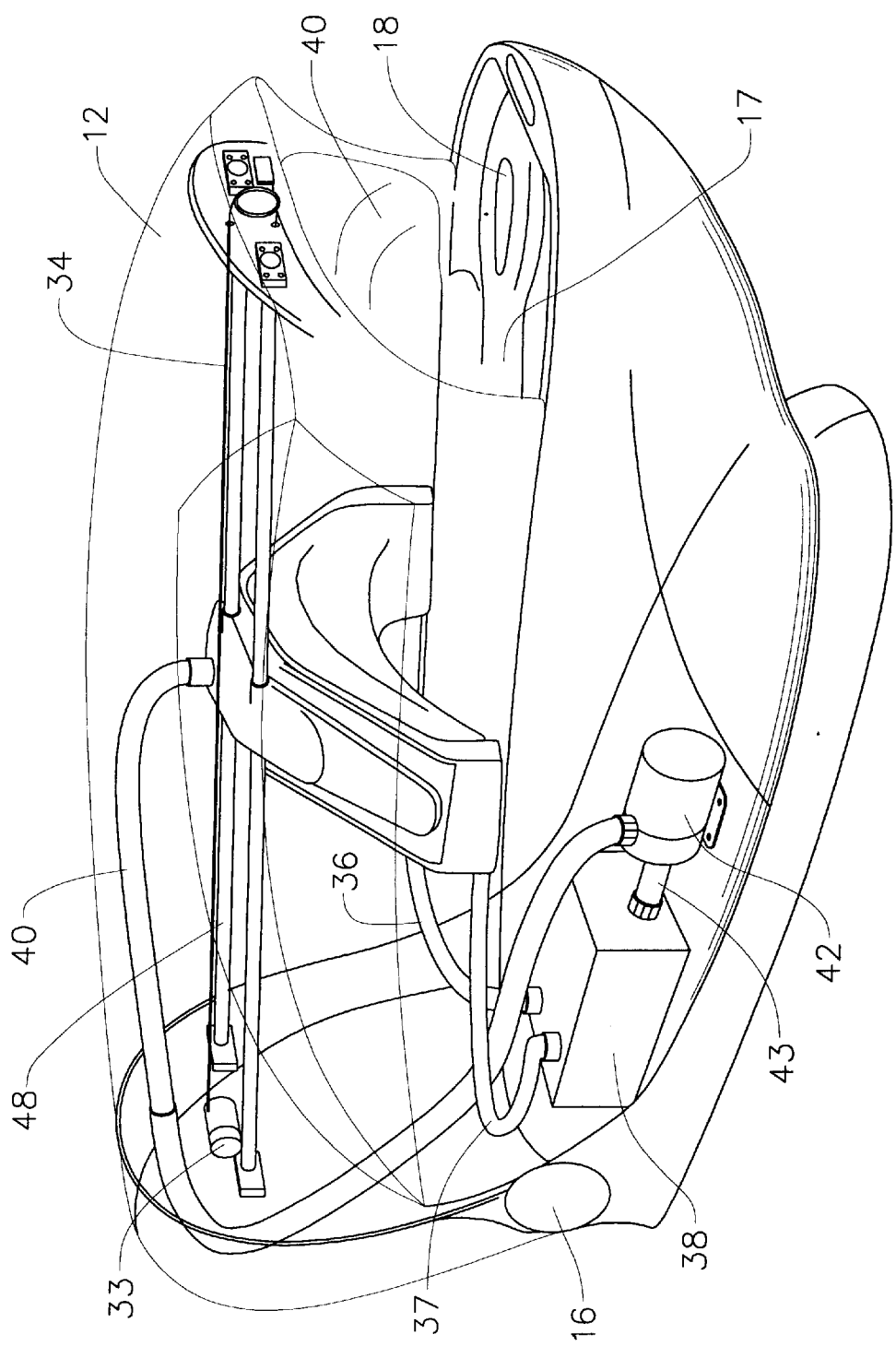
FIG. 3 shows another perspective with the lid in phantom lines.

In FIGS. 2 and 3, the bed 17 is shown inclined from a lower foot end to a higher head end. The foot end of the bed is designed with a space 20 to receive the feet of a prone person below the end of the bed in a natural posture. The aperture 18 also provides a padded support surface around the face without placing stress on the neck and back.

Figure 4:
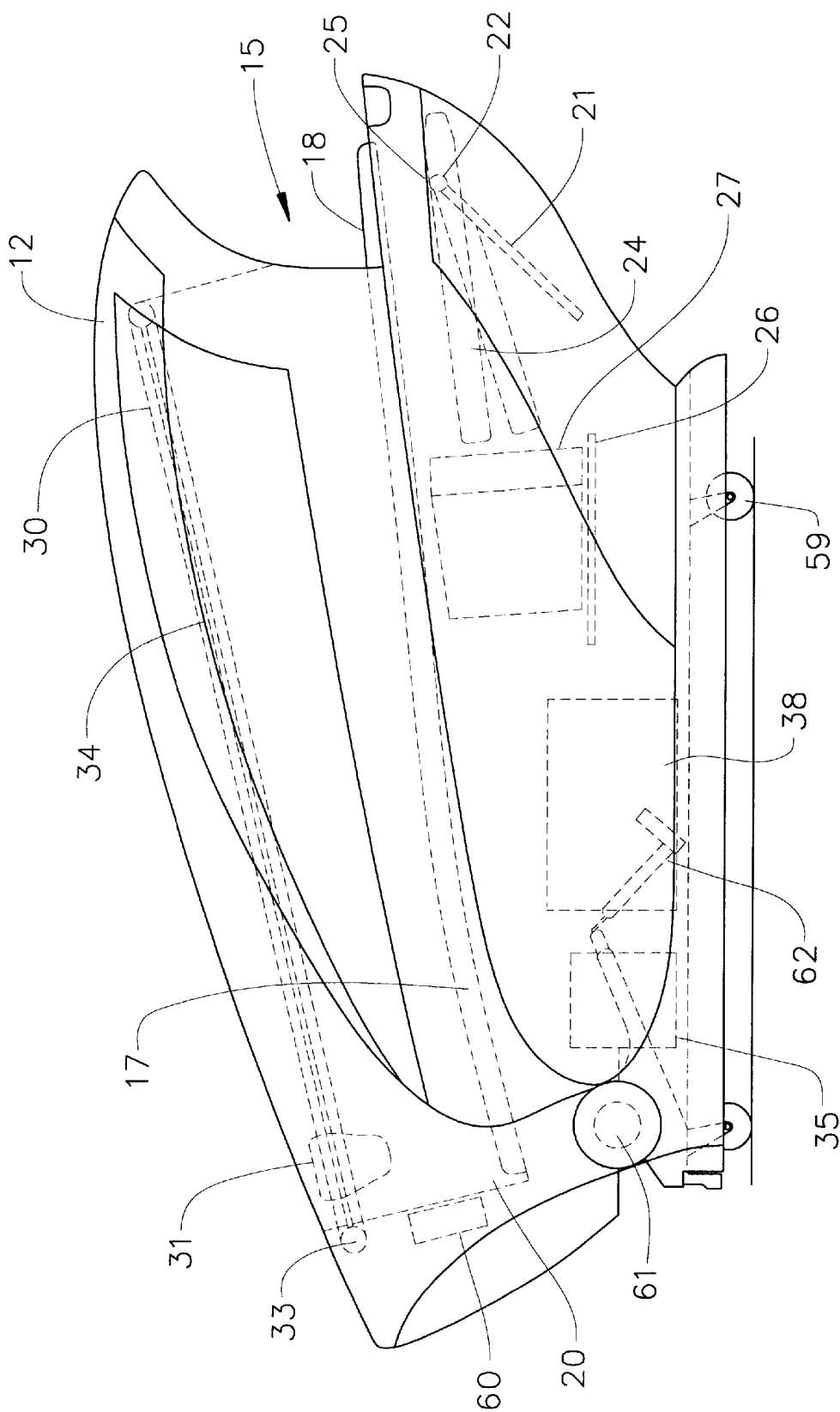
FIG. 4 shows a side view with interior components in phantom lines.

As shown in FIG. 4, under the aperture 18 is a mirror 21 which has a hinge connection 22 to the arm rests 23 and 24. The mirror 21 has a rotational adjustment 25 on either end of the hinge to change the angle of the mirror about the hinge 22. Mounted on shelf 26 of the cabinet 11 is an electronic screen 27. This device may be a conventional TV set or a CRT (cathode ray tube) or an LCD (liquid crystal display) connected to a tuner or VCR controlled inside the cabinet or outside or both. By adjusting the angle of the mirror different sized prone persons may view selected visual images.

The cabinet 11 and lid 12 may have multiple audio speakers 28 or a headphone jack 29. The speakers or headphones may be powered by components inside the spa (not shown) or may be connected to a sound system outside the spa. In any event, the person inside the spa may select the sounds to be transmitted to the spa. The selection may be done by a channel selector on the bed (not shown) or the sounds may be preselected before entry into the spa 10.

The lid 12 has a support system 30 extending throughout the major portion of it's length. An array 31 of nozzles 32 is suspended from this support system 30. The array 31 moves back and forth along the length of the support system 30 by a motorized pulley 33 and endless flexible drive 34. The control of the array and nozzles may be a simple timing device or a microprocessor 60. As the array moves lengthwise, the nozzles 32 deliver pulses of fluid into the enclosed space. The nozzles may be opened and closed to deliver the pulses or the pulses may be delivered through open nozzles by a pressure pump 35. The speed of the movement of the array and the timing of the pulses may be preselected to include a particular pattern or random application. Also, the operation of the nozzles, within the array, may be preselected.

The fluid may be a liquid or gas and the fluid may be scented or contain aromatic ingredients. The spa may also have receptacles for vials of aromatic substances. The vials may emit various fragrances to simulate different natural environments or particular scents desired by the user.

In the event the fluid is a liquid, the cabinet may have a thin fabric or film shroud 40 to be placed over the user. The longitudinal edges of the shroud may be attached to the sides of the bed 17 to seal the components of the spa.

Figure 5:
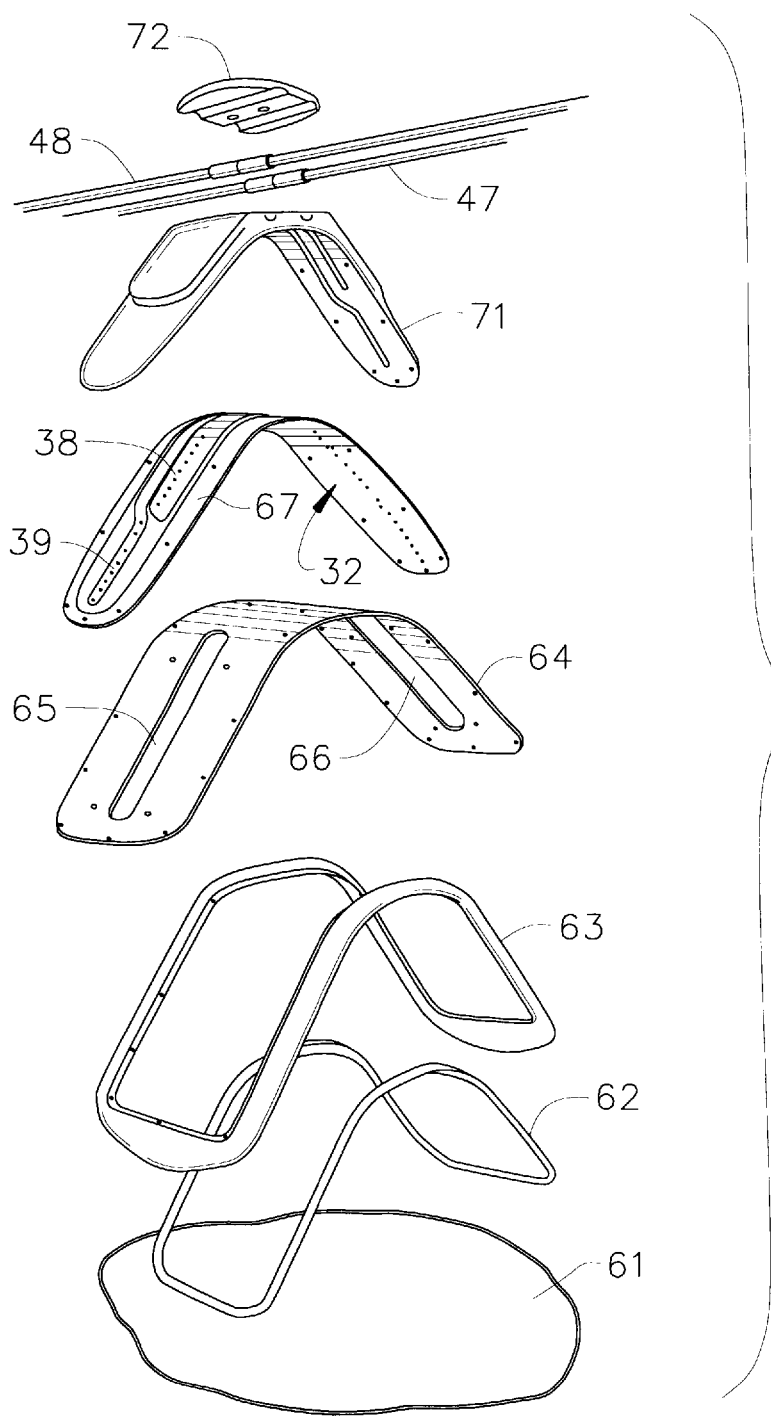
FIG. 5 shows an exploded view of the fluid array.

As illustrated in FIGS. 2, 3, and 5, the massage liquid is separated from the user by a thin, flexible, impervious liner 61 continuously sealed to the outer ring 63 by intermediate retainer ring 62. A rigid curved plastic plate 64 maintains the shape of the outer ring 63 and the retainer ring 62. The plate 64 has large openings 65 and 66 to permit passage of the massage liquid therethrough. The plate 64 is sealed to the lower jet housing 67 and the nozzles 32 are exposed through the openings 65 and 66. The lower jet housing 67 is connected to the upper jet housing 68 through a high pressure seal. The upper jet housing is connected to the liquid supply line 40. The upper jet housing contains a distribution channel 71 connecting the liquid inlet to the nozzles in the lower jet housing 67. The upper jet housing is slidably attached to the support system 30 by a cap 72, as shown in FIG. 5.

The massage liquid is removed from the lower portions of the array 31 by drain lines 36 and 37 and returned to the holding tank 38 for recycling. If recycling is not desired, the holding tank 38 may be connected to a drain. Depending on the installation, the spa may be used, without the impervious liner 61, in a manner that permits the fluid to impact directly on the skin of the user.

In FIGS. 2 and 3, the array 31 has a set of inner nozzles 38 and outer nozzles 39. The supply line 40 is connected to a fluid pump 42 which supplies pressure for the liquid jets. The pump 42 is connected to the holding tank 38 by a short connector 43. The supply line and the drain lines each have a length to accommodate the greatest travel of the array 31.

Figure 6:
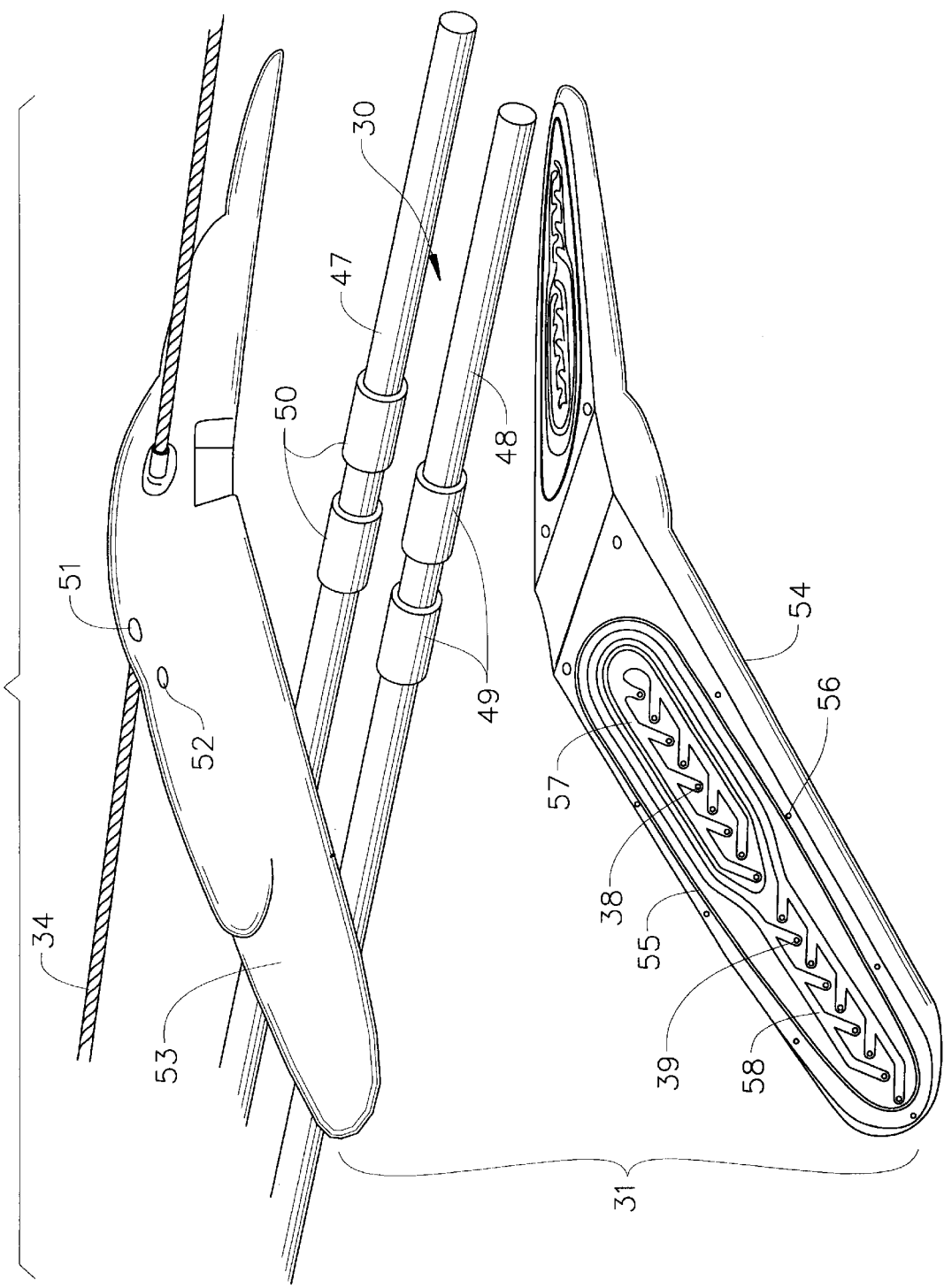
FIG. 6 shows an exploded view of the fluid head.

The flexible drive 34, shown in FIG. 6, moves the array 31 along the support system 30 which is formed with rods 47 and 48 suspended from the interior of the lid 12. The array slides along the rods on bearings 49 and 50. The flexible fluid supply lines are not shown but the connection to the array is at the ports 51 and 52. The upper section 53 of the array is sealed with the lower section 54 by O rings 55. The upper and lower sections are fastened together by fasteners 56. The inner nozzles 38 and outer nozzles 39 are shown as supplied by separate channels 57 and 58 formed in the array.

The spa of this invention may be used in health clubs, hospitals, assisted care facilities, hotels, other places of business, and the home. The user would select among the different features of the machine to develop a favorite combination of sights, sounds, smells, and massage. Once inside the spa, the user would only need to relax.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A spa capsule partially enclosing a person's body to provide a simulated environment by stimulating the optic senses comprising an elongated cabinet having a foot and a head end, said cabinet having an elongated lid, said cabinet and lid forming an enclosed space, said lid open at said head end, said cabinet including means for including visual images within said enclosed space, a bed located in said cabinet, said bed having an aperture therethrough to accommodate the face of a person in the prone position, an optical system below said bed to put said visual images in view of said prone person.

2. A spa capsule of claim 1 wherein said cabinet and said lid are connected together by a hinge at said foot end, said hinge permitting said lid to pivot away from said cabinet to open said enclosed space.

3. A spa capsule of claim 2 wherein said cabinet is mounted on casters for movement of said spa.

4. A spa capsule of claim 3 wherein said cabinet includes a bed extending from said head end to said foot end for supporting a person thereon.

5. A spa capsule of claim 4 wherein said elongated lid is of substantially the same length as same elongated cabinet.

6. A spa capsule of claim 1 wherein said cabinet includes means for stimulating the auditory senses by conveying certain sounds into said enclosed space.

7. A spa capsule of claim 1 wherein said cabinet includes means for stimulating the auditory and optic senses by conveying certain sounds and certain visual images into said enclosed space.

8. A spa capsule of claim 7 wherein said means for stimulating said olfactory, auditory and optic senses operate sequentially and in various sequences.

9. A spa capsule of claim 7 wherein said means for stimulating said olfactory, auditory and optic senses operate simultaneously.

10. A spa capsule of claim 6 wherein said means for stimulating said auditory senses includes speakers located in said cabinet operatively connected to a source of selectable sounds.

11. A spa capsule of claim 10 wherein said means for stimulating said auditory senses includes headphones.

12. A spa capsule of claim 1 wherein said means for stimulating said optic senses includes an electronic screen, said screen operatively connected to a source of visual images.

13. A spa capsule of claim 12 wherein said electronic screen is located in said cabinet and includes an optical system to put said screen in view of said person.

14. A spa capsule of claim 7 wherein said cabinet includes means for stimulating the tactile senses by modifying heat and light in said enclosed space.

15. A spa capsule of claim 14 wherein said means for stimulating said tactile senses includes message mechanism that applies pressure to specific points on the body, said pressure being momentary and repetitive.

16. A spa capsule of claim 1 wherein said optical system comprises a means for generating visual images and an adjustment means for changing the angle for viewing said visual images.

17. A spa capsule partially enclosing a person's body to provide a simulated environment by stimulating the auditory, olfactory, optic and tactile senses of the body comprising a cabinet having a head end and a foot end, said cabinet having a lid hingedly connected at said foot end, said cabinet and said lid forming an enclosed space, said lid open at said head end, said cabinet having means for selectively producing sounds, odors, visual images and massage in said enclosed space wherein each sense may be stimulated in sequence or simultaneously, said means for massage includes a movable array of fluid nozzles mounted in said enclosed space, said array intermittently connected to a supply of pressurized fluid producing pulses of fluid pressure in said enclosed space, a controller operatively connected to said array and said supply to control movement of said array and fluid flow to said nozzles, wherein said means for massage includes a plastic liner surrounding said fluid nozzles and movable therewith, said plastic liner connected to a drain mechanism extending from said liner to a holding tank, said holding tank connected to said supply of pressurized fluid for recycling of said fluid.

18. A spa capsule of claim 17 wherein longitudinal rods are connected to said lid extending from said head end to said foot end, said movable array of fluid nozzles are suspended from said rods for longitudinal movement in said enclosed space, said movable array including a plate for maintaining the shape of said plastic liner, said plate attached at the periphery to said plastic liner.

19. A spa capsule of claim 17 wherein said fluid is a liquid.

* * * * *